United States Patent
Zheng et al.

(10) Patent No.: US 11,986,346 B2
(45) Date of Patent: May 21, 2024

(54) GEL PAD FOR ULTRASOUND IMAGING

(71) Applicant: Telefield Medical Imaging Limited, Hong Kong (CN)

(72) Inventors: Yongping Zheng, Hong Kong (CN); Queenie Tsung Kwan Shea, Hong Kong (CN)

(73) Assignee: Telefield Medical Imaging Limited, Hong Kong (CN)

( * ) Notice: Subject to any disclaimer, the term of this patent is extended or adjusted under 35 U.S.C. 154(b) by 630 days.

(21) Appl. No.: 17/250,000

(22) Filed: Mar. 22, 2021

(65) Prior Publication Data
US 2022/0296214 A1   Sep. 22, 2022

(51) Int. Cl.
*A61B 8/00*   (2006.01)
*A61B 90/00*   (2016.01)

(52) U.S. Cl.
CPC ............ *A61B 8/4281* (2013.01); *A61B 90/39* (2016.02); *A61B 2090/3925* (2016.02)

(58) Field of Classification Search
CPC ..... A61B 8/4281; A61B 8/4272; A61B 90/39; A61B 2090/3925
See application file for complete search history.

(56) References Cited

U.S. PATENT DOCUMENTS

2012/0238859 A1*  9/2012  Tokita ................. A61B 5/0095
                                                       600/407
2015/0182189 A1   7/2015  Mullen

FOREIGN PATENT DOCUMENTS

WO   2020168087 A1   8/2020
WO   2020219705 A1   10/2020

* cited by examiner

*Primary Examiner* — Amelie R Davis
(74) *Attorney, Agent, or Firm* — S&F/WEHRW

(57) ABSTRACT

A gel pad for facilitating ultrasound scanning between an ultrasound transducer and a skin surface is provided. The gel pad has a first surface being bendable with a small degree and maintained locally flat, and a second surface being more bendable than the first surface for contacting the skin surface. A coupling media is arranged between the first and second surface with a stiffness gradient increasing from the second surface to the first surface. The first surface is capable of facilitating the ultrasound transducer to move swiftly on the gel pad. The second surface is capable of conforming to a non-uniform shape of the skin surface. On the first or second surface, position markers are provided for determining coordinates of the ultrasound transducer, by blocking ultrasound signals from transmitting through the gel pad to generate dark strips or marks in the ultrasound images.

18 Claims, 8 Drawing Sheets

GEL PAD FOR ULTRASOUND IMAGING

FIELD OF THE INVENTION

The present disclosure generally relates to a gel pad for facilitating ultrasound scanning, and particularly relates to a gel pad having a more deformable surface for fitting on an irregularly shaped body surface.

BACKGROUND OF THE INVENTION

Ultrasound imaging uses sound waves to create two-dimensional or three-dimensional images of anatomical structures, such as tendons, muscles, joints, blood vessels, and internal organs. This can be used for various medical diagnostic purposes. In particular, obstetric ultrasound is a standard procedure of prenatal care. Ultrasound imaging by manual or mechanical scanning on the surface of the body could be very difficult. Typically, ultrasound gel, which is in a semi-liquid form, is placed between the scanning surface of the body and the ultrasound transducer. The ultrasound gel enables the ultrasound to be transmitted efficiently into the body for scanning the body tissues. However, the skin surface of the body is in complex geometry, a direct contact between the ultrasound transducer and the skin surface may be difficult to guarantee. Moreover, air gaps may occur between the transducer and the skin surface during scanning or imaging, which may affect the accuracy and precision of the measurement due to the poor ultrasound coupling (impedance matching) between the air and the transducer.

For ultrasound scanning on a geometrically complex skin surface, for example, the back of the body with protruded spinous processes, a large amount of ultrasound gel is needed to fill the gap between the body surface and the ultrasound transducer. However, even if a large amount of gel is used, it is still challenging as the amount of gel needed in different area of the surface could be different. The operator must ensure the gel is always enough by regularly adding more gels during the ultrasound scanning. This is particularly difficult when ultrasound imaging is conducted on a large surface area. Air gaps often exist between the ultrasound transducer and the body surface, which causes undesirable disruption to the scanned image. In some cases, loss or distortion due to the poor acoustic coupling between the ultrasound transducer and the body surface may create inaccurate images, rendering an erroneous medical diagnosis. There are gel pads available for ultrasound scanning, which are normally in regular shapes, such as a rectangular or disk shape with certain uniformed thickness. These gel pads are uniform about their bending capability and are used to serve as coupling media between ultrasound transducer and the skin surface so that the use of gel can be reduced or avoided. However, such gel pads are not designed for the application with large irredularly shpared skin surface of a human body.

Accordingly, there is a need in the art for a gel pad that seeks to address at least some of the above problems by providing a deformable surface for fitting on the irregularly shaped skin surface of a human body. Furthermore, other desirable features and characteristics will become apparent from the subsequent detailed description and the appended claims, taken in conjunction with the accompanying drawings and this background of the disclosure.

SUMMARY OF THE INVENTION

Provided herein is a gel pad for facilitating ultrasound scanning for producing clear ultrasound images.

In accordance with certain aspect of the present disclosure, a gel pad comprises a first surface being bendable with a small degree and maintained locally flat, and a second surface being more bendable than the first surface for contacting the skin surface. A coupling media is arranged between the first and second surface with a stiffness gradient increasing from the second surface to the first surface. The second surface is capable of conforming to a non-uniform shape of the skin surface. The first surface is capable of facilitating the ultrasound transducer to move swiftly on the gel pad.

According to certain aspects, the coupling media comprises a base component and a cross-linker component having a concentration gradually increasing from the second surface to the first surface.

According to certain aspects, the base component is a water-based material, silicone, or Polydimethylsiloxane (PDMS).

Preferably, the base component is silicone and the cross-linker component is a silicone catalyst, and a low and a high concentration ratios of the base component to the cross-linker component are selected from a range between 100:1 to 1:1.

According to certain aspects, the coupling media comprises two or more coupling materials of different stiffness adhesively attached together to form the stiffness gradient.

According to certain aspects, the first surface comprises a locally curved surface for conforming to a shape of the ultrasound transducer.

According to certain aspects, the second surface comprises one or more adhesive areas for fixing the gel pad on the skin surface.

According to certain aspects, the gel pad further comprises a plurality of position markers for determining coordinates of the ultrasound transducer. The plurality of position markers is arranged to block ultrasound signals from transmitting through the gel pad and generate dark strips or marks in the ultrasound images.

In one embodiment, the plurality of position markers is arranged in a row or a column for tracking a 1-dimensional position of the ultrasound transducer. In another embodiment, the plurality of position markers is arranged in rows and columns to form a 2-dimensional grid for tracking a 2-dimensional position of the ultrasound transducer.

According to certain aspects, each of the plurality of position markers is made of a material with a different acoustic impedance from the gel pad.

Preferably, the material is selected from the group consisting of air bubble, oil drop, metal wire, polyethylene, polyvinylidene fluoride, and polyethylene terephthalate.

According to certain aspects, each of the plurality of position markers has a shape selected from the group consisting of a cross shape and a spherical dot, thereby a high visibility is maintained in the ultrasound images.

According to certain aspects, the coupling media is dry-able to a reduced shape for easy storage and transportation, and is restorable to an original shape by absorbing water.

In accordance with a further aspect of the present disclosure, a gel pad comprises a first surface being bendable with a small degree and maintained locally flat for contacting the ultrasound transducer, a permeable second surface for contacting the skin surface, a first gel section comprising a semi-liquid form ultrasound gel, and a second gel section for storing water or gel. The first gel section and the second gel section are arranged between the first surface and the permeable second surface. The permeable second surface is more bendable than the first surface, such that the permeable second surface is capable of conforming to a non-uniform shape of the skin surface, and the first surface is capable of facilitating the ultrasound transducer to move swiftly on the first surface.

According to certain aspects, the permeable second surface comprises a plurality of liquid-permeable holes capable of permitting the water or the gel to be squeezed out or naturally flown out from the second gel section.

In accordance with a further aspect of the present disclosure, an automated system for performing ultrasound scanning of a predetermined area for producing ultrasound images is provided. The automated system comprises an ultrasound transducer, a gel pad placed between the ultrasound transducer and a skin surface, and a mechanical system for conveying the ultrasound transducer along the gel pad based on the coordinates of the ultrasound transducer. The gel pad comprises a first surface being bendable with a small degree and maintained locally flat for contacting the ultrasound transducer, a second surface being more bendable than the first surface and capable of conforming to a non-uniform shape of the skin surface, a coupling media having a stiffness gradient increasing from the second surface to the first surface, and a plurality of position markers on the first surface, the second surface, or inside the coupling media for indicating the coordinates of the ultrasound transducer.

According to certain aspects, the plurality of position markers is arranged to block ultrasound signals from transmitting through the gel pad and generate dark strips or marks in the ultrasound images. The automated system determines a coordinate of the ultrasound transducer based on the dark strips or marks in the ultrasound images. The mechanical system conveys the ultrasound transducer within the predetermined area for performing ultrasound scanning.

According to certain aspects, the mechanical system comprises one or more conveyor belts driven by one or more rollers and/or gears to convey the ultrasound transducer.

According to certain aspects, each of the plurality of position markers is made of a material with a different acoustic impedance from the gel pad.

According to certain aspects, the automated system comprises a computer system connected to the ultrasound transducer and the mechanical system via a cable.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which.

DETAILED DESCRIPTION OF THE INVENTION

Figure 1:
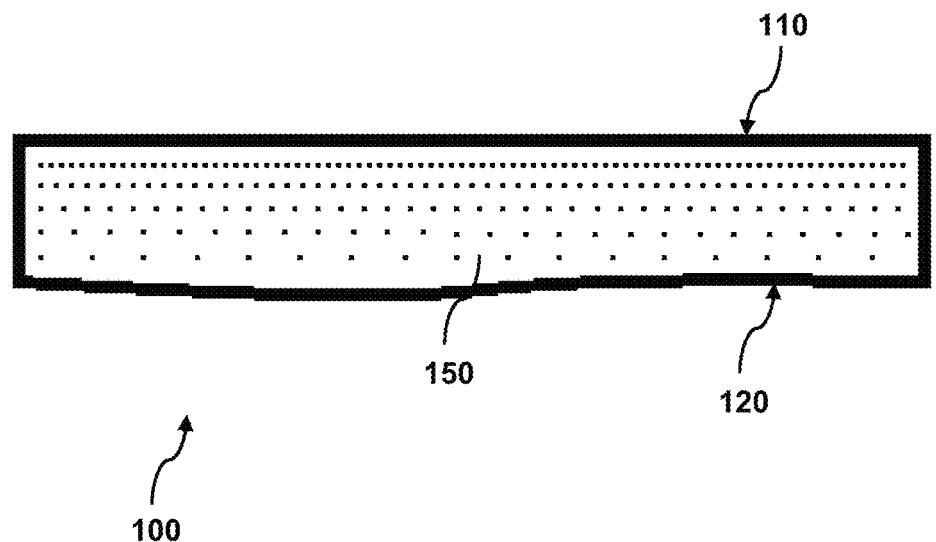
FIG. 1 is a cross-sectional side view of a gel pad in accordance with certain embodiments of the present disclosure.

The present disclosure generally relates to a gel pad for facilitating ultrasound scanning. More specifically, but without limitation, the present disclosure relates to a gel pad having a deformable surface for fitting on an irregularly shaped body surface. An objective of the present disclosure is to maximize the accuracy and precision of the ultrasonic imaging by providing direct contact between the ultrasound transducer and the skin surface without using a large amount of ultrasound gel.

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The benefits, advantages, solutions to problems, and any element(s) that may cause any benefit, advantage, or solution to occur or become more pronounced are not to be construed as critical, required, or essential features or elements of any or all of the claims. The invention is defined solely by the appended claims including any amendments made during the pendency of this application and all equivalents of those claims as issued.

For simplicity and clarity, relational terms such as "first," "second," and the like, are used solely to distinguish one from another entry, item, or device, without necessarily requiring any actual such relationship or order between such entries, items, or devices.

As used herein, terms such as "local" and "global", and any variants thereof, are used to refer to a two-dimensional body part or surface. "Local" refers to the dimension that is comparable or smaller than the contact area of a typical ultrasound transducer, which is generally less than 10 cm in length. "Global", when used in conjunction with terms such as area or curve, refers to the area or curve of a typical ultrasound transducer with a dimension equal to or larger than 10 cm.

The term "gel pad" is used herein as a descriptive and inclusive term to mean a pad having the described characteristics even though "gel" may not be used in the pad. The gel pad may be made of different sizes and different thicknesses depending on the application.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The use of any and all examples, or exemplary language (e.g., "such as") provided herein, is intended merely to illuminate the invention better and does not pose a limitation on the scope of the invention unless the claims expressly state otherwise. Recitation of ranges of values herein is merely intended to serve as a shorthand method of referring individually to each separate value falling within the range, unless otherwise indicated herein, and each separate value is incorporated into the specification as if it were individually recited herein. Furthermore, as used herein, the term "about" or "approximately", when used in conjunction with a numerical value or range of values, refers preferably to a range that is within 10 percent, preferably within 5 percent, or more preferably within 1 percent of the value with which the term is associated. No language in the specification should be construed as indicating any non-claimed element as essential to the practice of the invention.

Figure 2:
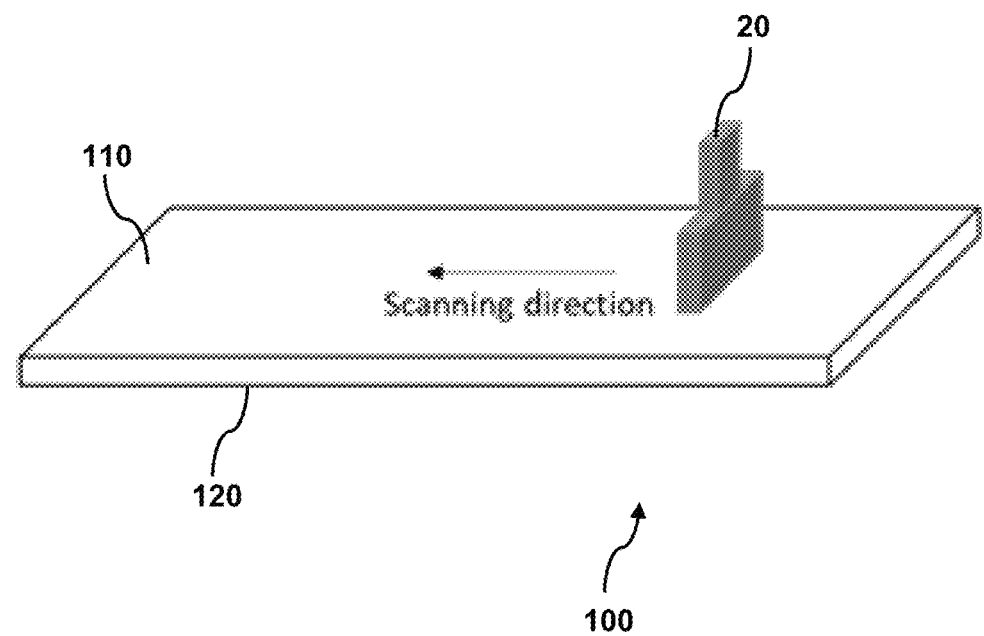
FIG. 2 is a conceptual diagram depicting the use of an ultrasound transducer probe on the gel pad of FIG. 1 for performing ultrasound scanning.

FIG. 1 conceptually illustrates a cross-sectional side view of a gel pad 100 for coupling ultrasound from an ultrasound transducer probe into the human body in accordance with certain embodiments of the present disclosure. FIG. 2 illustrates the use of an ultrasound transducer probe 20 on the gel pad 100. In the illustrated embodiments, the gel pad 100 is rectangular in shape. It is apparent that the gel pad 100 may be in other shapes without departing from the scope and spirit of the present disclosure. The gel pad 100 comprises a first surface 110, a second surface 120, and a coupling media 150. The first surface 110 is used in direct contact with the contact face of the ultrasound transducer 20, while the second surface 120 is used in direct contact with the skin surface. The gel pad 100 is used to replace the conventional ultrasound gel for enabling the ultrasound to be transmitted efficiently into the human body for scanning the body tissues.

The human body has a complex geometry on the skin surface. It is not easy to develop a universal media for transmitting ultrasound into the human body for medical or imaging purposes. The aim of the present disclosure is to provide a novel media for transmitting the sound wave into the body with reduced air between the skin surface and the ultrasound transducer. Advantageously, the first surface 110 is smooth and relatively flatter, with a locally fixed shape. In order to maintain the smoothness, the first surface 110 is less locally deformable, and can only allow a small degree of deformation to generally fit on the skin surface when placed on the human body with global curvatures. For example, the gel pad 100 can be placed around the waist, around the thigh, or on the back even when the human body is in a bending position. The first surface 110 is only bendable with a small degree and maintained locally flat for contacting the ultrasound transducer 20, such that the first surface 110 is capable of facilitating the ultrasound transducer 20 to move swiftly on the gel pad 100. The second surface 120 is soft and allows a high degree of deformation that can be in direct contact with the skin surface, which displaces air from between the gel pad 100 and the skin surface and conforms to a non-uniform shape of the skin surface. Therefore, the second surface 120 is more bendable than the first surface 110, and can be shaped according to the body shape. The second surface 120 can change dynamically with the body surface as the body posture changes, thereby no air gap is left between the skin surface and the second surface 120. Therefore, a clear ultrasound image can be produced without acoustic impedance reduction or reflection.

Between the first surface 110 and the second surface 120, a coupling media 150 is provided for transmitting ultrasound signals. The coupling media 150 has an acoustic property which allows ultrasound to transmit through the thickness of the coupling media 150 with minimal attenuation. This can be achieved by selecting materials that intrinsically have low ultrasound attenuation. In certain embodiments, the coupling media 150 has an acoustic impedance level similar to that of the skin, which can minimize the reflection of ultrasound across the boundary between the skin surface and the coupling media 150. Preferably, the gel pad 100 has little or no deterioration in acoustic impedance during storage.

In certain embodiments, the coupling media 150 has a stiffness gradient increasing from the second surface 120 to the first surface 110. Therefore, the coupling media 150 closer to the second surface 120 is more deformable in order to conform to a non-uniform shape of the skin surface. Likewise, the coupling media 150 closer to the first surface 110 is less deformable and relatively flatter, which permits the ultrasound transducer 20 to move along a scanning direction smoothly.

In certain embodiments, the coupling media 150 comprises a base component and a cross-linker component. The cross-linker component has the concentration controlled and gradually increased from the second surface 120 to the first surface 110. In certain embodiments, the base component is a water-based material, silicone, or Polydimethylsiloxane (PDMS). Preferably, the base component is silicone, and the cross-linker component is a silicone catalyst. The concentration ratio of the base component to the cross-linker component is increased gradually from a low concentration ratio to a high concentration ratio. In certain embodiments, the low and high concentration ratios of the base component to the cross-linker component are selected from a range between 100:1 to 1:1. In one embodiment, the low concentration ratio is approximately 50:1, and the high concentration ratio is approximately 30:1. The gradual increase in concentration may base on a function selected from a group consisting of linear, piecewise linear, exponential, piecewise exponential, and any combination thereof. In certain embodiments, the coupling media 150 is dryable to a reduced shape for easy storage and transportation, and is restorable to an original shape by absorbing water.

Alternatively, the coupling media 150 may comprise two or more coupling materials of different stiffness to form the stiffness gradient. The two or more coupling materials are contacted with each other in a manner that is adhesively attached together to form the coupling media 150 with stiffness gradient. For example, the two or more coupling materials include the same base component but with two or more different concentrations of cross-linker components.

Figure 3:
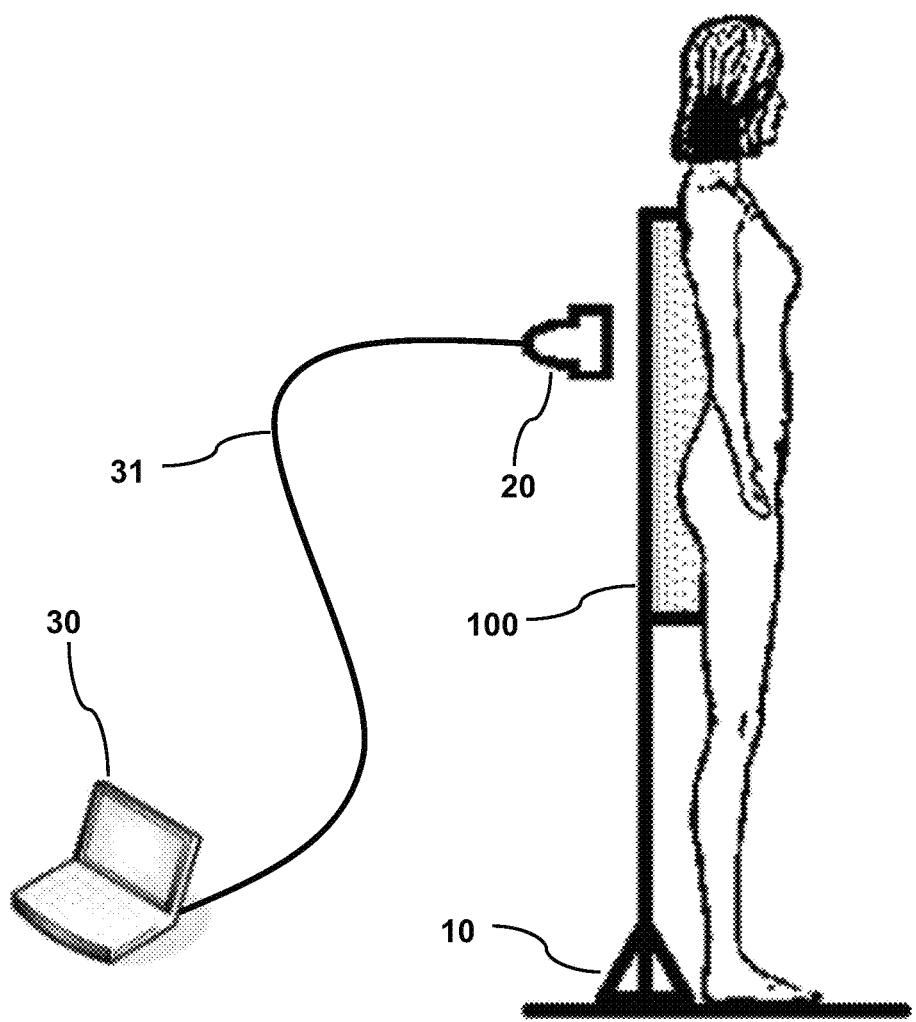
FIG. 3 depicts a side view of a person receiving ultrasound scanning at the back using the gel pad of FIG. 1.

FIG. 3 illustrates a side view of a person receiving ultrasound scanning at the back using the gel pad 100. The ultrasound transducer 20 is connected to a computer system 30 or an imaging system via a cable. The gel pad 100 for scanning the back of a person at a standing position can be very heavy. To avoid any negative effect on the body posture caused by the extra weight bearing, the gel pad 100 is hanged or supported by a stand 10 such that the gel pad 100 can be placed next to the person without added weight to the person. The ultrasound transducer 20 can be moved swiftly on the first surface 110 of the gel pad 100 for capturing the ultrasound images. With the second surface 120, the gel pad 100 can also contact the skin surface of the person by conforming to the non-uniform shape.

Figure 4A:
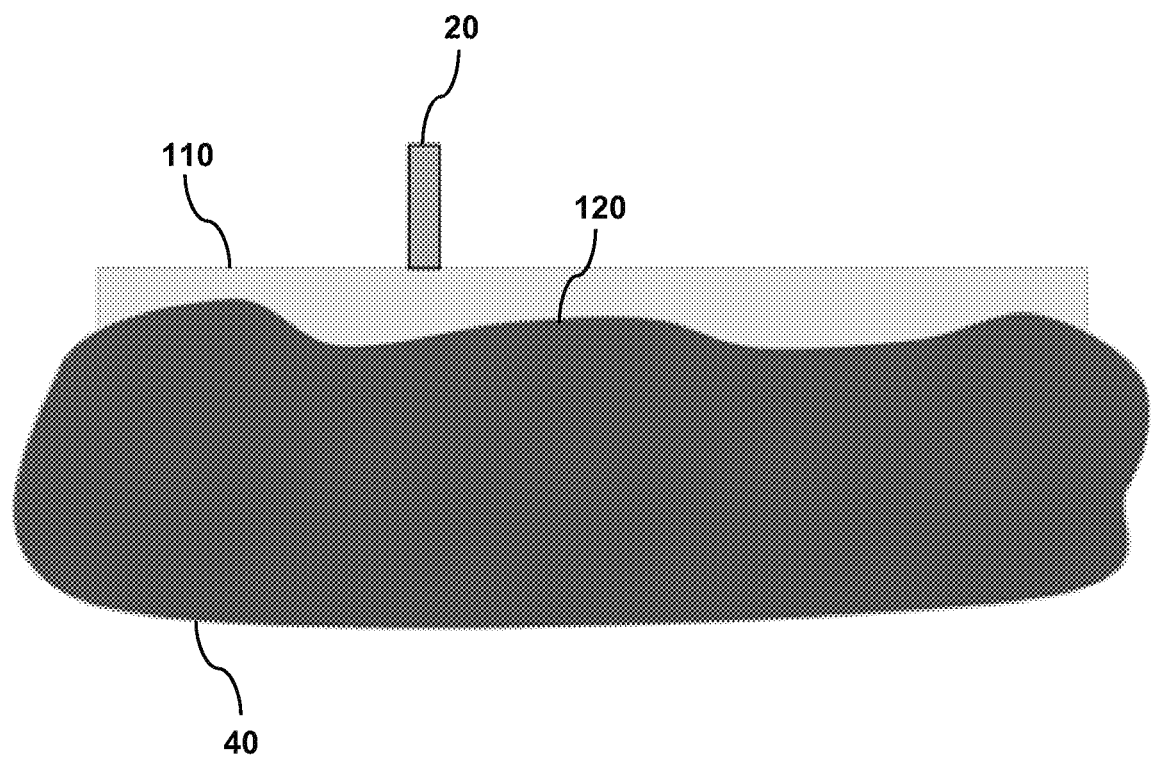
FIG. 4A is a conceptual diagram depicting the use of the gel pad of FIG. 1 on an irregularly shaped body surface.
Figure 4B:
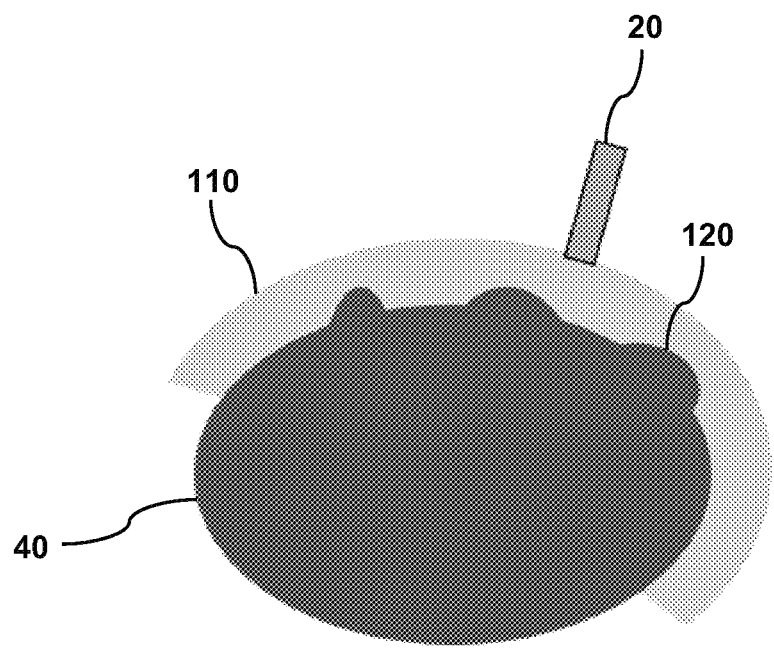
FIG. 4B is a conceptual diagram depicting the use of the gel pad of FIG. 1 on another irregularly shaped body surface.

FIGS. 4A and 4B are conceptual diagrams depicting the use of the gel pad 100 on irregularly shaped body surfaces. The body 40 may be a complex surface with non-uniform shape. The second surface 120 is fitted to the skin surface of the body 40, while the first surface 110 is maintained flat for ultrasound scanning. When the body 40 has a globally curved surface, the gel pad is deformed and slightly banded to fit exactly onto the skin surface of the body 40, while the first surface 110 is remained locally flat to facilitate ultrasound scanning.

Figure 5:
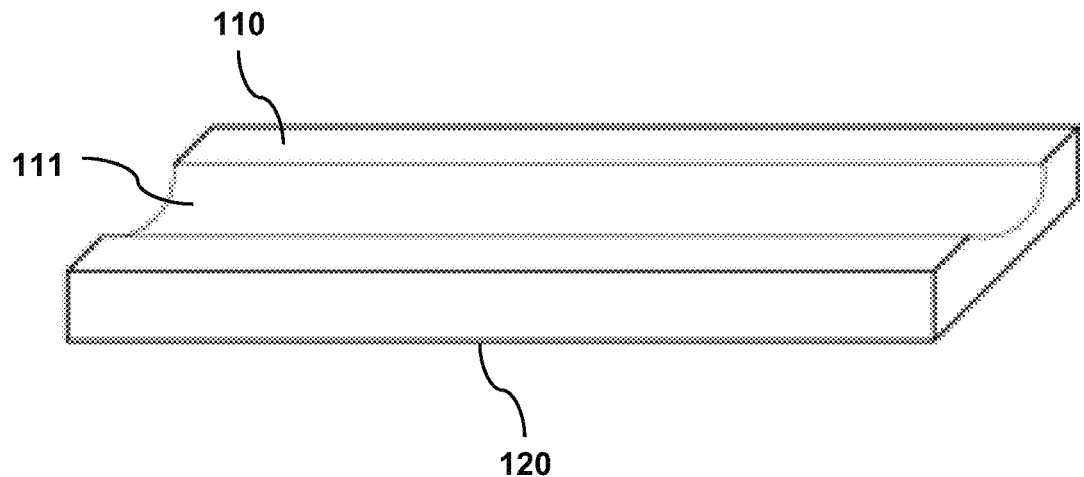
FIG. 5 is a perspective view of a gel pad having a curved top surface in accordance with certain embodiments of the present disclosure.

In certain embodiments, as illustrated in FIG. 5, the first surface 110 comprises a locally curved surface 111 for conforming to the shape of the ultrasound transducer. The locally curved surface 111 has a concave curvature, which can facilitate scanning using a curved ultrasound array.

Figure 6:
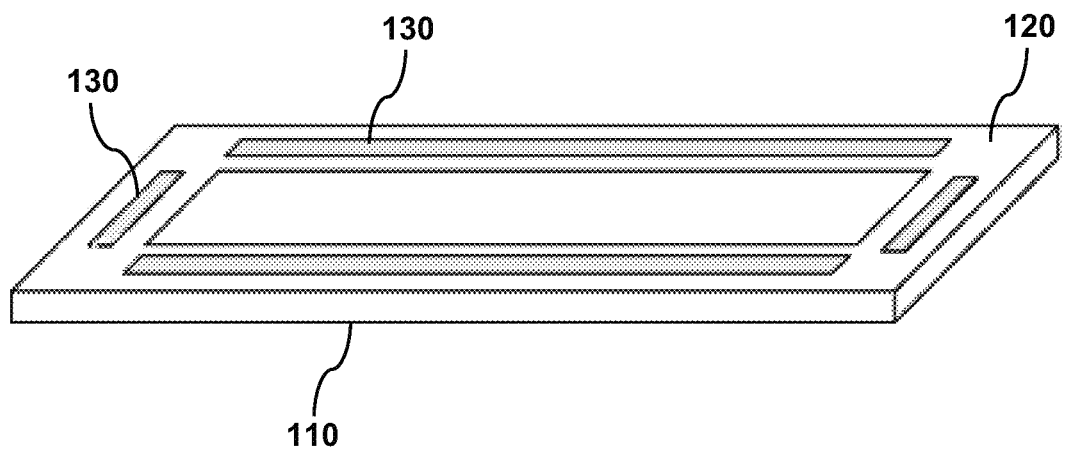
FIG. 6 is a perspective view of a gel pad having adhesive tapes on the bottom surface in accordance with certain embodiments of the present disclosure.

In certain embodiments, as illustrated in FIG. 6, the second surface 120 comprises one or more adhesive areas 130 for fixing the gel pad 100 on the skin surface. Alternatively, the second surface 120 can be entirely adhesive with high frictional resistance when in contact with the skin surface.

Figure 7:
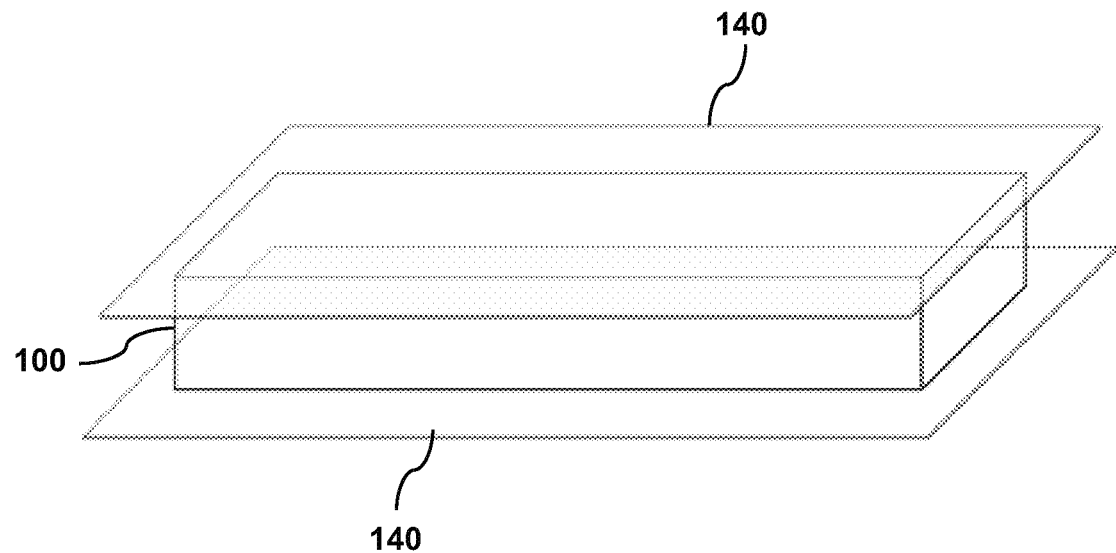
FIG. 7 is a perspective view of the gel pad of FIG. 1 covered by two thin plastic sheets for storage or transportation.

In certain embodiments, as illustrated in FIG. 7, the gel pad 100 can be covered by two thin plastic sheets 140 or membranes for storage or transportation, and peeled off when being used.

Figure 8A:
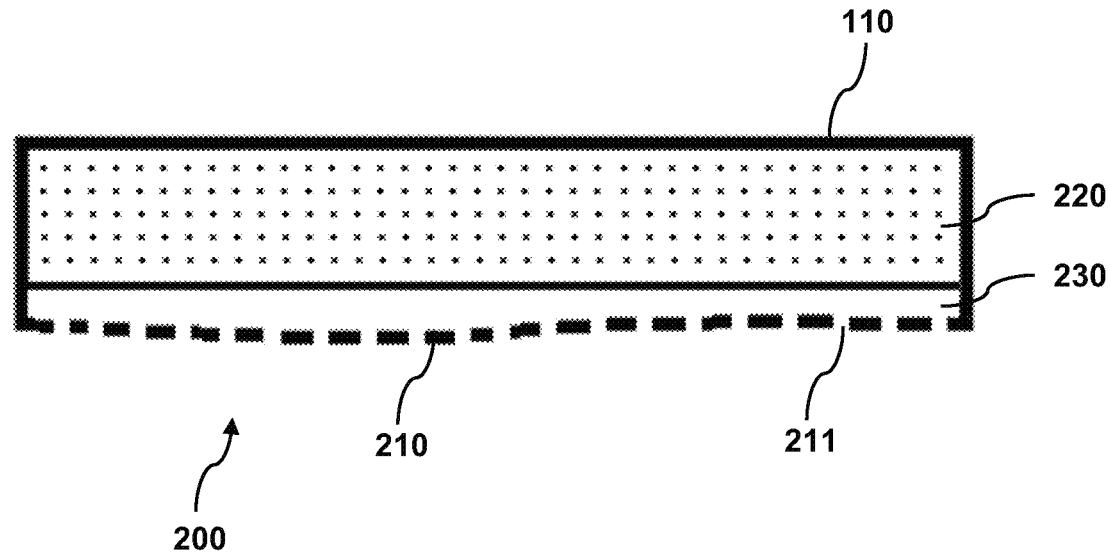
FIG. 8A is a cross-sectional side view of a gel pad having a permeable second surface in accordance with certain embodiments of the present disclosure.
Figure 8B:
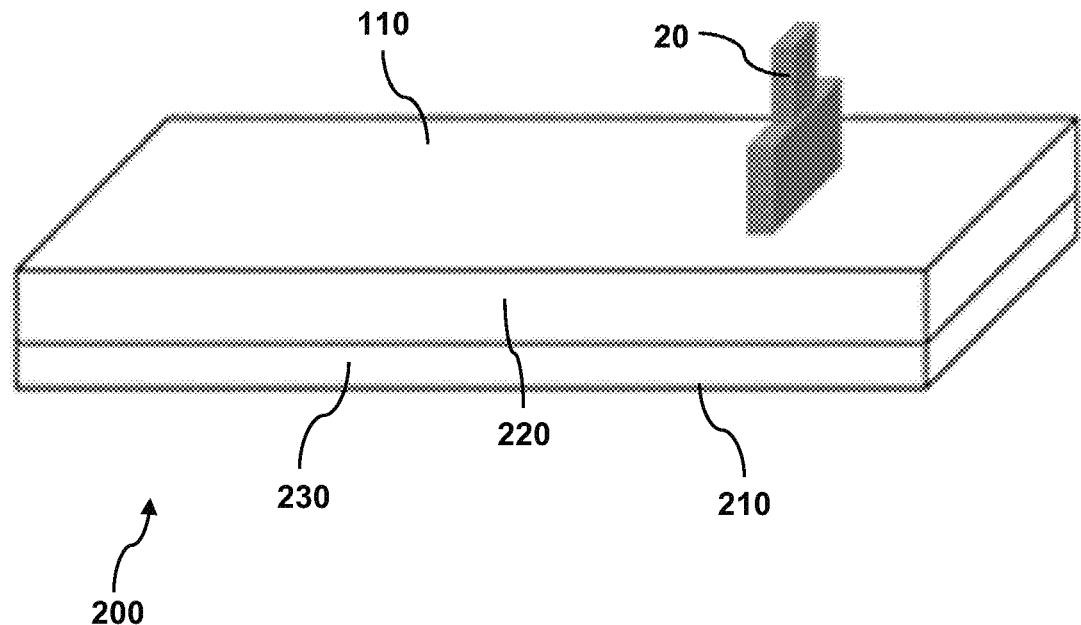
FIG. 8B is a conceptual diagram depicting the use of an ultrasound transducer probe on the gel pad of FIG. 8A for performing ultrasound scanning.

In accordance with a second aspect of the present invention, a gel pad 200 of an alternative structure is provided for facilitating ultrasound scanning between an ultrasound transducer 20 and a skin surface for producing clear ultrasound images. FIG. 8A conceptually illustrates a cross-sectional side view of the gel pad 200, and FIG. 8B illustrates the use of an ultrasound transducer probe 20 on the gel pad 200. The gel pad 200 comprises a first surface 110, a permeable second surface 210, a first gel section 220, and a second gel section 230. The first surface 110 may be a plastic sheet, which is bendable with a small degree and maintained locally flat for contacting the ultrasound transducer 20. The permeable second surface 210 is more bendable than the first surface 110, and is used in direct contact with the skin surface. The first gel section 220 and second gel section 230 are arranged between the first surface 110 and the permeable second surface 210 to enable the ultrasound to be transmitted efficiently into the human body for scanning the body tissues. The permeable second surface 210 is capable of conforming to a non-uniform shape of the skin surface, and the first surface 110 is capable of facilitating the ultrasound transducer 20 to move swiftly on the first surface 110.

Figure 8C:
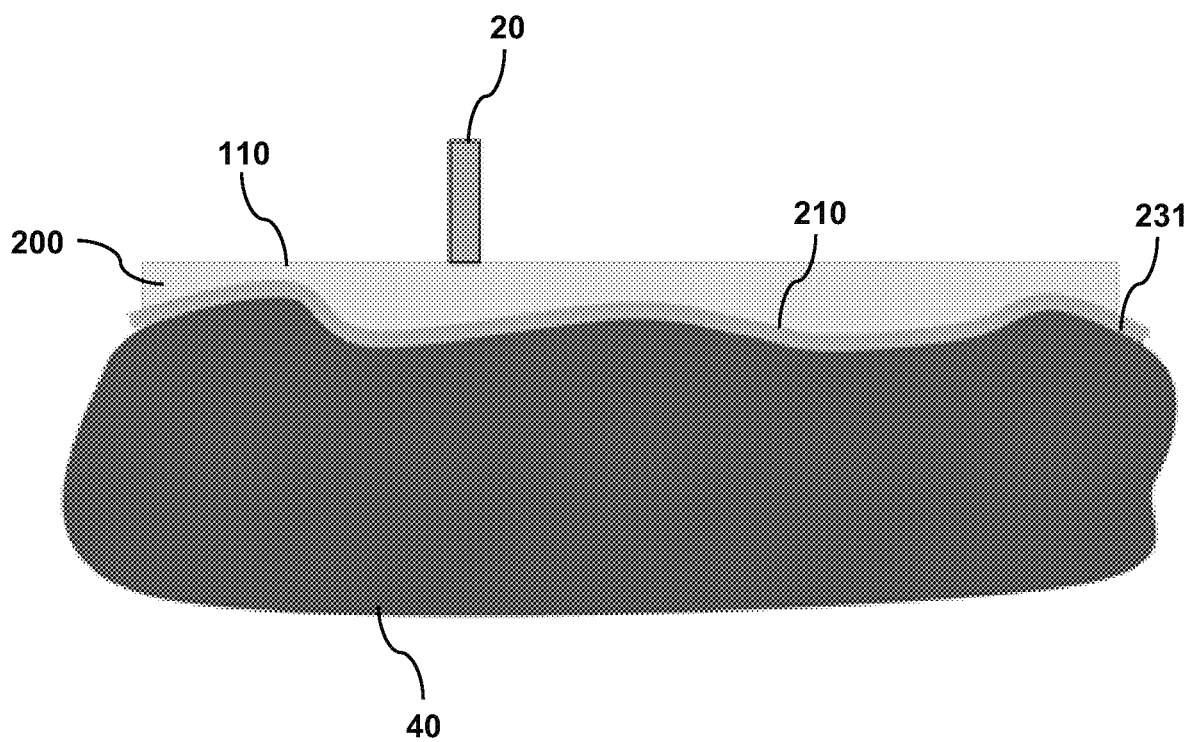
FIG. 8C is a conceptual diagram depicting the use of the gel pad of FIG. 8A on an irregularly shaped body surface.

The permeable second surface 210 is arranged to store water or gel. Advantageously, the permeable second surface 210 comprises a plurality of liquid-permeable holes 211 capable of permitting the water or the gel to be squeezed out by a gentle force or naturally flown out from the second gel section 230. As conceptually illustrated in FIG. 8C, the water or the gel squeezed out from the second gel section 230 forms an intermediate layer 231 between the body 40 and the gel pad 200, which can maximize the contact of the permeable second surface 210 of the gel pad 200 to the skin surface. Therefore, the permeable second surface 210 can be in good contact with the body 40. Furthermore, during storage and transportation, the gel pad 200 can be dried to reduce the size and weight thereof. Before using, the gel pad 200 can be immersed into water to absorb sufficient water to make the second gel section filled with water for working status.

A third aspect of the present invention provides a gel pad 300 having a plurality of position markers 160 and an automated system for performing ultrasound scanning for producing clear ultrasound images. The plurality of position markers 160 is provided for determining coordinates of the ultrasound transducer 20 for tracking the position.

Figure 9A:
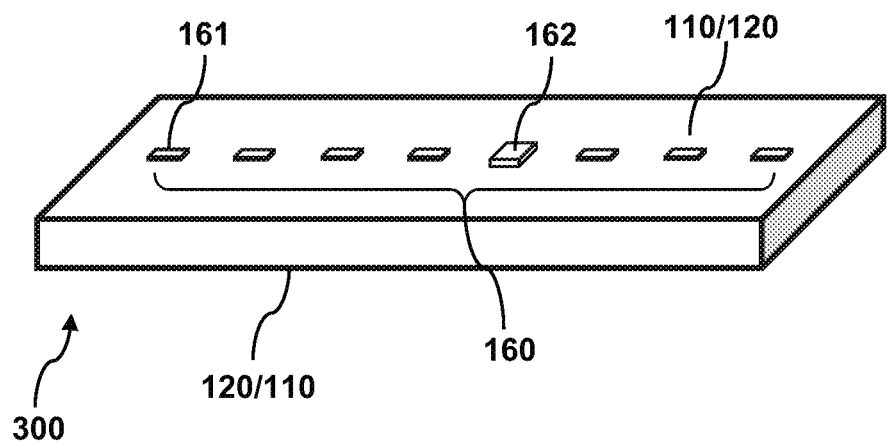
FIG. 9A is a perspective view of a gel pad having a plurality of 1-dimensional position markers in accordance with certain embodiments of the present disclosure.
Figure 9B:
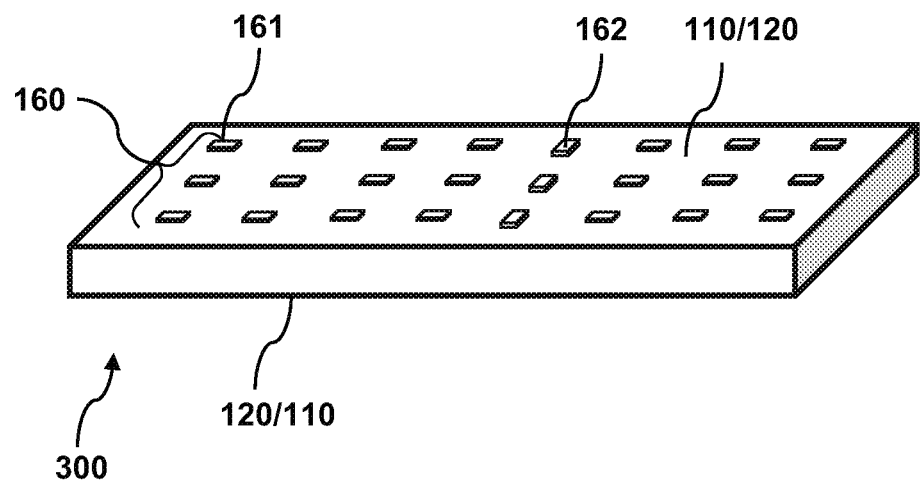
FIG. 9B is a perspective view of a gel pad having a plurality of 2-dimensional position markers in accordance with certain embodiments of the present disclosure.

As illustrated in FIG. 9A, the plurality of position markers 160 may be arranged in a row or a column, preferably with small markers 161 and large markers 162, for tracking a 1-dimensional position of the ultrasound transducer 20. Similarly, as illustrated in FIG. 9B, the plurality of position markers 160 may be arranged in rows and columns to form a 2-dimensional grid, preferably with small markers 161 and large markers 162, for tracking a 2-dimensional position of the ultrasound transducer 20. The plurality of position markers 160 may be provided on the first surface 110, the second surface 120, or inside the coupling media 150 without departing from the spirit of the present disclosure.

As will be described in greater detail below, each of the plurality of position markers 160 is made of a material with a different acoustic impedance from the gel pad 300. In certain embodiments, the material is selected from the group consisting of air bubble, oil drop, metal wire, polyethylene, polyvinylidene fluoride, and polyethylene terephthalate. In certain embodiments, each of the plurality of position markers 160 has a shape selected from the group consisting of a cross shape and a spherical dot, thereby the overall ultrasound images captured by the ultrasound transducer 20 have high visibility. Therefore, the plurality of position markers 160 can block the ultrasound signals from transmitting through the gel pad 300 and generate dark strips or marks in ultrasound images. The small markers 161 and the large markers 162 can respectively generate dark strips or marks of different sizes, which can further be used to precisely locate the position of the ultrasound transducer 20. This is particularly important for enabling an automated system for performing ultrasound scanning automatically.

Figure 10:
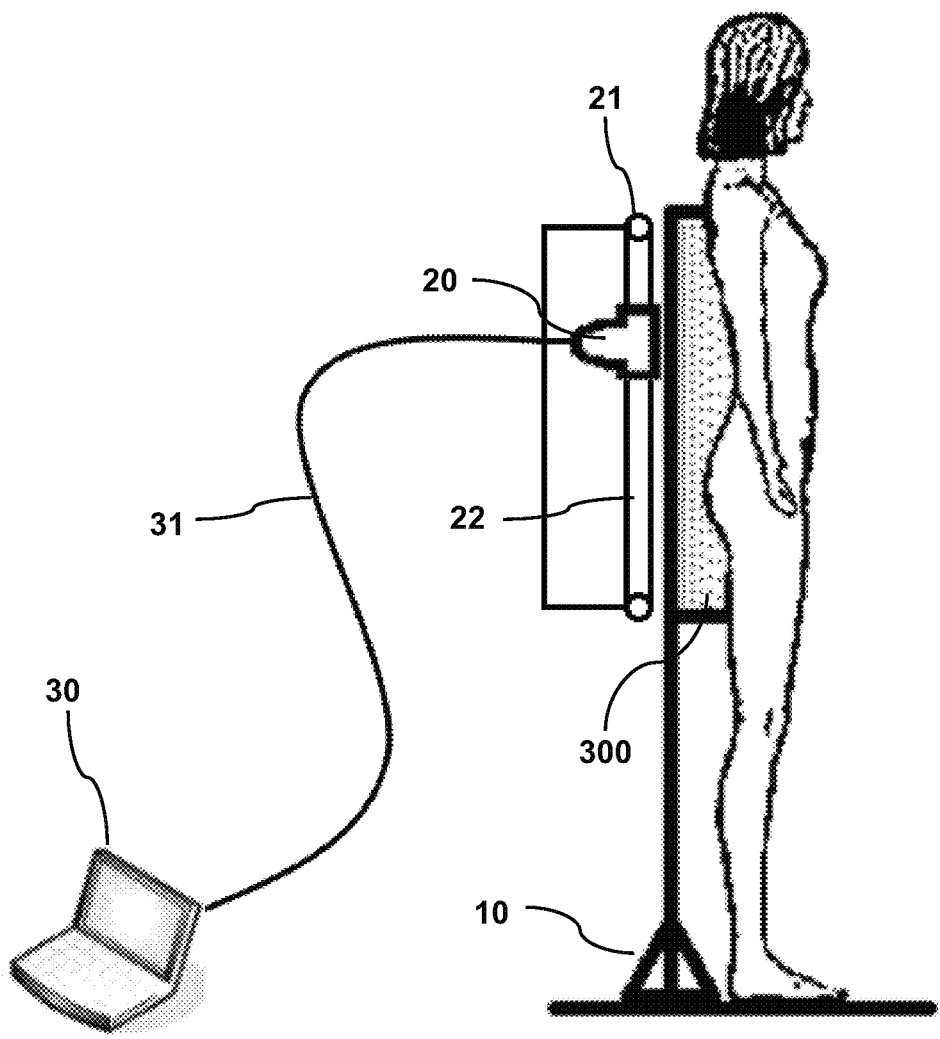
FIG. 10 depicts a side view of a person receiving ultrasound scanning at the back using an automated system in accordance with certain embodiments of the present disclosure.

FIG. 10 is a side view of a person receiving ultrasound scanning at the back using an automated system. The ultrasound transducer 20 is connected to a computer system 30 via a cable 31. In the illustrated embodiment, the gel pad 300 is hanged or supported by a stand 10 or a mechanical frame, such that the gel pad 300 can be placed next to the person without added weight to the person. The first surface of the gel pad 300 is bendable with a small degree and maintained locally flat, thereby the ultrasound transducer 20 can be moved swiftly on the first surface 110 of the gel pad 300 for capturing the ultrasound images. The second surface 120 is more bendable than the first surface 110 such that the second surface 120 is capable of conforming to a non-uniform shape of the skin surface. The ultrasound transducer 20 is movable on the gel pad 300 by a mechanical system, which is controlled by the computer system 30 via a cable 31. The plurality of position markers 160 on the first surface 110, the second surface 120, or inside the coupling media 150 can be identified by the computer system 30 for determining the coordinates of the ultrasound transducer 20. In comparison, other conventional scanning approaches, such as using ultrasound gel, cannot guarantee a smooth and flat surface for setting up an automated system.

In particular, the plurality of position markers 160 is arranged to block the ultrasound signals from transmitting through the gel pad 300 and generate dark strips or marks in ultrasound images. Based on the dark strips or marks in the ultrasound images, the computer system 30 determines a coordinate of the ultrasound transducer 20. The ultrasound scanning for a predetermined area is generally predefined by sets of coordinates, so the coordinates of the ultrasound transducer 20 as determined can be used to control the movement of the ultrasound transducer 20, whereas the computer system 30 can log each ultrasound image captured with the corresponding coordinates. The computer system 30 controls the mechanical system to convey the ultrasound transducer 20 along the gel pad 300 within the predetermined area based on the coordinates of the ultrasound transducer 20 for performing ultrasound scanning. In certain embodiments, the mechanical system comprises one or more conveyor belts 22 mounted on a stand 10 or a mechanical frame, which are driven by one or more rollers 21 and/or gears to convey the ultrasound transducer 20. The speed of the one or more rollers 21 can be controlled with high precision based on the coordinates. Other movement mechanisms may also be employed instead of the conveyor belts 22 without departing from the scope and spirit of the present disclosure.

This illustrates the fundamental structure of the gel pad in accordance with the present disclosure. It will be apparent that variants of the above-disclosed and other features and functions, or alternatives thereof, may be combined into many other different systems or applications. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

What is claimed is:

1. A gel pad for facilitating ultrasound scanning between an ultrasound transducer and a skin surface for producing ultrasound images, the gel pad comprising:
   a first surface being bendable with a small degree and maintained locally flat for contacting the ultrasound transducer;
   a second surface for contacting the skin surface; and
   a coupling media having a stiffness gradient increasing from the second surface to the first surface,
   wherein the second surface is more bendable than the first surface, such that the second surface is capable of conforming to a non-uniform shape of the skin surface, and the first surface is capable of facilitating the ultrasound transducer to move swiftly on the gel pad, wherein the gel pad further comprises a plurality of position markers for determining coordinates of the ultrasound transducer, wherein the plurality of position markers is arranged to block ultrasound signals from transmitting through the gel pad and generate dark strips or marks in the ultrasound images.

2. The gel pad of claim 1, wherein the coupling media comprises a base component and a cross-linker component having a concentration gradually increasing from the second surface to the first surface.

3. The gel pad of claim 2, wherein the base component is a water-based material, silicone, or Polydimethylsiloxane (PDMS).

4. The gel pad of claim 2, wherein the base component is silicone and the cross-linker component is a silicone catalyst, and a low and a high concentration ratios of the base component to the cross-linker component are selected from a range between 100:1 to 1:1.

5. The gel pad of claim 1, wherein the coupling media comprises two or more coupling materials of different stiffness adhesively attached together to form the stiffness gradient.

6. The gel pad of claim 1, wherein the first surface comprises a locally curved surface for conforming to a shape of the ultrasound transducer.

7. The gel pad of claim 1, wherein the second surface comprises one or more adhesive areas for fixing the gel pad on the skin surface.

8. The gel pad of claim 1, wherein the plurality of position markers is arranged in a row or a column for tracking a 1-dimensional position of the ultrasound transducer.

9. The gel pad of claim 1, wherein the plurality of position markers is arranged in rows and columns to form a 2-dimensional grid for tracking a 2-dimensional position of the ultrasound transducer.

10. The gel pad of claim 1, wherein each of the plurality of position markers is made of a material with a different acoustic impedance from the gel pad.

11. The gel pad of claim 10, wherein the material is selected from the group consisting of air bubble, oil drop, metal wire, polyethylene, polyvinylidene fluoride, and polyethylene terephthalate.

12. The gel pad of claim 1, wherein each of the plurality of position markers has a shape selected from the group consisting of a cross shape and a spherical dot, thereby a high visibility is maintained in the ultrasound images.

13. The gel pad of claim 1, wherein the coupling media is dryable to a reduced shape for easy storage and transportation, and is restorable to an original shape by absorbing water.

14. A gel pad for facilitating ultrasound scanning between an ultrasound transducer and a skin surface for producing ultrasound images, the gel pad comprising:
   a first surface being bendable with a small degree and maintained locally flat for contacting the ultrasound transducer;
   a permeable second surface for contacting the skin surface;
   a first gel section comprising a semi-liquid form ultrasound gel; and
   a second gel section for storing water or gel, wherein;
   the first gel section and the second gel section are arranged between the first surface and the permeable second surface, and
   the permeable second surface is more bendable than the first surface, such that the permeable second surface is capable of conforming to a non-uniform shape of the skin surface, and the first surface is capable of facilitating the ultrasound transducer to move swiftly on the first surface, wherein the gel pad further comprises a plurality of position markers for determining coordinates of the ultrasound transducer, wherein the plurality of position markers is arranged to block ultrasound signals from transmitting through the gel pad and generate dark strips or marks in ultrasound images.

15. The gel pad of claim 14, wherein the permeable second surface comprises a plurality of liquid-permeable holes capable of permitting the water or the gel to be squeezed out or naturally flown out from the second gel section.

16. An automated system for performing ultrasound scanning of a predetermined area for producing ultrasound images, the automated system comprising:
an ultrasound transducer;
a gel pad placed between the ultrasound transducer and a skin surface, wherein the gel pad comprises:
a first surface being bendable with a small degree and maintained locally flat for contacting the ultrasound transducer;
a second surface being more bendable than the first surface and capable of conforming to a non-uniform shape of the skin surface;
a coupling media having a stiffness gradient increasing from the second surface to the first surface; and
a plurality of position markers arranged on the first surface, the second surface, or inside the coupling media for indicating coordinates of the ultrasound transducer;
and
a mechanical system for conveying the ultrasound transducer along the gel pad, wherein:
the plurality of position markers is arranged to block ultrasound signals from transmitting through the gel pad and generate dark strips or marks in the ultrasound images; and
the automated system determines the coordinates of the ultrasound transducer based on the dark strips or marks in the ultrasound images, and controls the mechanical system to convey the ultrasound transducer within the predetermined area for performing ultrasound scanning.

17. The automated system of claim 16, wherein the mechanical system comprises one or more conveyor belts driven by one or more rollers and/or gears to convey the ultrasound transducer.

18. The automated system of claim 16, wherein each of the plurality of position markers is made of a material with a different acoustic impedance from the gel pad.

* * * * *